（12）United States Patent
Loescher et al.

(10) Patent No.: US 7,145,049 B2
(45) Date of Patent: Dec. 5, 2006

(54) OLIGOMERIZATION PROCESS

(75) Inventors: Mitchell E. Loescher, Houston, TX (US); David G. Woods, Baytown, TX (US); Michael J. Keenan, Baton Rouge, LA (US); Steven E. Silverberg, Baytown, TX (US); Paul W. Allen, Baton Rouge, LA (US)

(73) Assignees: Catalytic Distillation Technologies, Pasadena, TX (US); Exxonmobil Chemical Patents, Inc., Baytown, TX (US)

( * ) Notice: Subject to any disclaimer, the term of this patent is extended or adjusted under 35 U.S.C. 154(b) by 141 days.

(21) Appl. No.: 10/898,506

(22) Filed: Jul. 23, 2004

(65) Prior Publication Data

US 2005/0049448 A1 Mar. 3, 2005

Related U.S. Application Data

(60) Provisional application No. 60/489,977, filed on Jul. 25, 2003.

(51) Int. Cl.
C07C 2/04 (2006.01)
C07C 2/02 (2006.01)

(52) U.S. Cl. ............ 585/533; 585/510; 585/520; 585/530; 585/532

(58) Field of Classification Search ........... 585/510, 585/520, 530, 532, 533
See application file for complete search history.

(56) References Cited

U.S. PATENT DOCUMENTS

| 3,960,978 A | 6/1976 | Givens et al. ...... 260/683.15 R |
| 4,021,502 A | 5/1977 | Plank et al. ........ 260/683.15 R |
| 4,150,062 A | 4/1979 | Garwood et al. ........... 260/673 |
| 4,211,640 A | 7/1980 | Garwood et al. ........... 208/255 |
| 4,227,992 A | 10/1980 | Garwood et al. ............. 208/46 |
| 4,242,530 A | 12/1980 | Smith, Jr. .................... 585/510 |
| 4,334,113 A | 6/1982 | Pellegrini, Jr. et al. ....... 585/18 |
| 4,375,576 A | 3/1983 | Smith, Jr. .................... 585/510 |
| 4,377,393 A | 3/1983 | Schleppinghoff ............... 44/53 |
| 4,447,668 A | 5/1984 | Smith, Jr. et al. ........... 585/639 |
| 4,463,211 A | 7/1984 | Manning ..................... 585/510 |
| 4,720,600 A | 1/1988 | Beech, Jr. et al. .......... 585/330 |
| 4,935,577 A * | 6/1990 | Huss et al. .................. 585/726 |
| 4,950,834 A | 8/1990 | Arganbright et al. ....... 585/446 |
| 5,003,124 A | 3/1991 | Smith, Jr. et al. ........... 585/526 |
| 5,113,034 A | 5/1992 | Soled et al. ................. 585/510 |
| 5,324,878 A | 6/1994 | Brunelli et al. ............. 585/508 |
| 5,510,555 A | 4/1996 | Brunelli et al. ............. 585/508 |
| 5,571,445 A | 11/1996 | Srinivasan et al. ......... 508/189 |
| 5,608,133 A | 3/1997 | Chang et al. ............... 585/524 |
| 5,610,112 A | 3/1997 | Lago et al. ................... 502/63 |
| 5,612,270 A | 3/1997 | Beck et al. ................... 502/64 |
| 5,639,931 A | 6/1997 | Hellring ..................... 585/722 |
| 5,670,681 A | 9/1997 | Kuber et al. .................. 556/53 |
| 5,877,372 A | 3/1999 | Evans et al. ................ 585/510 |
| 5,888,355 A | 3/1999 | Mikitenko et al. ..... 203/DIG. 6 |
| 5,986,158 A * | 11/1999 | Van Broekhoven et al. 585/722 |
| 6,143,942 A * | 11/2000 | Verrelst et al. ............. 585/533 |
| 6,166,279 A * | 12/2000 | Schwab et al. ............. 585/324 |

(Continued)

Primary Examiner—Glenn Caldarola
Assistant Examiner—In Suk Bullock
(74) Attorney, Agent, or Firm—Kenneth H. Johnson

(57) ABSTRACT

Alkenes, such as normal butenes in a mixed $C_4$ stream are oligomerized, preferably to dimers, which are dimerized in a distillation column reactor over ZSM-57 zeolite catalyst at high conversions and high selectivity to octenes. Prior to oligomerization the mixed $C_4$ stream is pretreated to remove dimethyl ether, butadienes and sulfur compounds.

18 Claims, 1 Drawing Sheet

U.S. PATENT DOCUMENTS

| | | | |
|---|---|---|---|
| 6,169,218 B1 * | 1/2001 | Hearn et al. | 585/260 |
| 6,274,783 B1 | 8/2001 | Gildert et al. | 585/255 |
| 6,596,913 B1 | 7/2003 | Loescher | 585/504 |
| 6,875,899 B1 * | 4/2005 | Martens et al. | 585/327 |
| 2004/0020758 A1 | 2/2004 | Wang et al. | 203/74 |

* cited by examiner

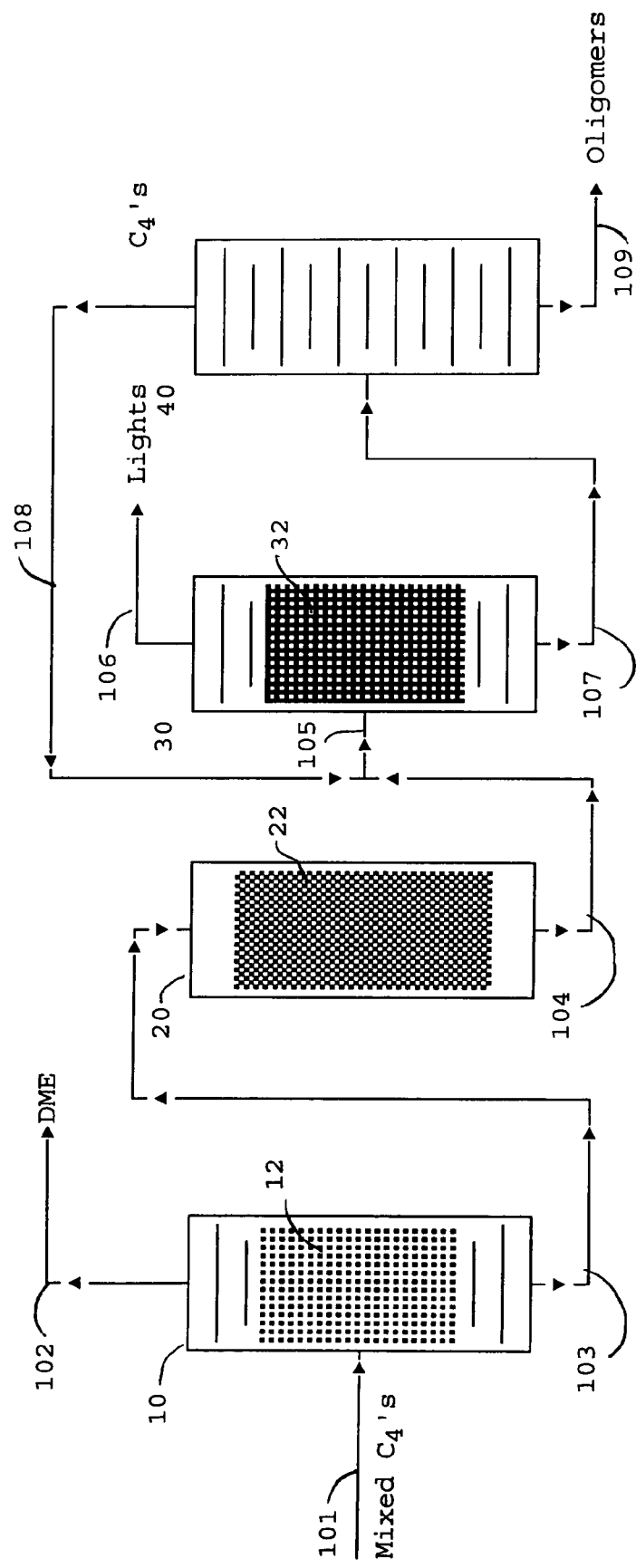

OLIGOMERIZATION PROCESS

This application claims the benefit of provisional application 60/489,977 filed Jul. 25, 2003.

BACKGROUND OF THE INVENTION

1. Field of the Invention

The present invention relates to the oligomerization of alkenes, e.g., the oligomerization of normal butenes to produce primarily octenes. More particularly the invention relates to the oligomerization of 1-butene and 2-butene contained in a mixed $C_4$ stream which has been depleted of isobutenes such as from an MTBE unit or isobutene purification units. More particularly the invention relates to the oligomerization of butenes over ZSM-57 zeolite catalyst in a distillation column reactor.

2. Related Art

The mixed $C_4$ stream from an MTBE unit or an isobutene purification unit, often called a raffinate stream, contains diluted normal butenes, especially butene-1 and butene-2. These streams have been dimerized in the past in tubular reactors containing catalysts such as supported phosphoric acid (SPA) and the zeolites ZSM-22 and ZSM-57. However the reaction conditions have been severe, e.g., temperatures of between 330° F. to 482° F. and pressures of between 1,000 psig to 1,215 psig.

Besides the reaction conditions the catalysts have previously had short lives. The SPA catalyst produces only about 333 tons of oligomers per ton of catalyst and has a useful lifetime of 2–3 weeks on stream, after which the catalyst must be discarded. The zeolite catalysts have longer lifetimes (3–4 months), but lose activity and must be regenerated off-line at considerable expense.

The selectivity of the above-mentioned catalysts is lower than ideal. The desired product from butenes is octenes, which can be converted to isononyl alcohols. Higher oligomers, such as $C_{12}$ olefins are useful to the extent that profitable outlets, e.g., tridecyl alcohol or isopar solvents, can be found.

Typical results of the selectivity of the above catalysts in the tubular reactors are shown below in TABLE I:

TABLE I

| | | Catalyst | | | |
| --- | --- | --- | --- | --- | --- |
| | SPA | ZSM-22 @ 94%* | ZSM-22 @ 50%* | ZSM-57 @ 94%* | ZSM-57 @ 50%* |
| Selectivity, Mol % | | | | | |
| Paraffin | <1 | 6 | 6 | <1 | <1 |
| $C_6$ Olefin | 1 | <1 | <1 | <1 | <1 |
| $C_7$ Olefin | 4 | <1 | <1 | <1 | <1 |
| $C_8$ Olefin | 45 | 50 | 70 | 78 | 88 |
| $C_9$ Olefin | 9 | 1.5 | <1 | 3 | <1 |
| $C_{10}$–$C_{11}$ Olefin | 13 | 2 | <1 | 1 | <1 |
| $C_{12}$ Olefin | 22 | 27 | 18 | 10 | 7 |
| $C_{12}$+ Olefin | 4 | 13 | 5 | 7 | 2 |

*Olefin conversion per pass

Finally, it should be noted that isobutenes have been oligomerized over acid cation exchange resin catalysts in distillation column reactors in combination with boiling point reactors as disclosed in U.S. Pat. Nos. 4,242,530 and 5,003,124.

The present invention provides higher conversion per pass than in other processes with higher selectivity. A further advantage is that the present process operates under less severe conditions of temperature and pressure than prior commercial oligomerization processes using ZSM-57 catalyst. Still another advantage is a much longer online time before turnaround to regenerate the catalyst and potentially longer catalyst life. It is a feature of the present invention that the catalyst can be regenerated and enhanced in situ, thus providing even greater efficiency and cost savings.

SUMMARY OF THE INVENTION

Briefly, the present invention is a process for the oligomerization of alkenes comprising feeding alkenes to a distillation column reactor containing a bed of ZSM-57 zeolite catalyst, contacting said alkenes with said ZSM-57 zeolite catalyst under conditions of oligomerization, thereby catalytically reacting said alkenes to form oligomers and concurrently separating and recovering said oligomers. Preferably the alkenes comprise linear alkenes having from 3 to 8 carbon atoms, such as $C_4$ alkenes, preferably n-butenes.

In a preferred embodiment the mixed butenes, such as raffinate, may be readily oligomerized over the zeolite catalyst ZSM-57 in a distillation column reactor at very high selectivity to octenes (>90 mol %). The oligomerization is preferably carried out under conditions which favor dimerization as opposed to longer chain oligomers, preferably at pressures of between 300 and 400 psig and temperatures in the range of 240 to 320° F. at conversions of up to about 97 mol %.

To obtain the advantages of the present process the mixed butenes must be free of certain components that poison the ZSM-57 catalyst such as dimethyl ether (DME), and some sulfur compounds, e.g., dimethyl sulfide, and butadiene. This is also required for the prior non catalytic distillation processes using ZSM-57. All of the undesirable materials can be removed conventionally by distillation, sulfur chemisorption and butadiene hydrogenation.

In cases where the sulfur guard bed has failed and sulfur compounds have poisoned the ZSM-57 catalyst, the catalyst may be regenerated in situ by washing with normal heptane. The regeneration has been found to have increased the catalyst activity.

BRIEF DESCRIPTION OF THE DRAWING

The FIGURE is a simplified flow diagram of the preferred embodiment of the invention.

DESCRIPTION OF THE PREFERRED EMBODIMENT

The feed to the present process is preferably pretreated to remove contaminants such as DME, butadiene and sulfur compounds. Acceptable levels of these impurities are: DME<1 wppm; total sulfur<1 wppm; and 1–3 butadiene<10 wppm. The DME can be removed by distillation which may be conveniently combined with the selective hydrogenation of the 1-3 butadiene in a distillation column reactor. A hydrogenation catalyst, such as palladium or nickel, is used in a distillation column reactor at mild conditions. The DME is taken as overheads and the remainder is taken as bottoms. The sulfur compounds may be removed by chemisorption on reduced massive nickel catalysts, such as Sud-Chemie C46 or Engelhard D-4130.

A typical feed to the process of the present invention comprises dilute normal butenes in a mixed $C_4$ stream which has typically been depleted of isobutene. Table II below lists the components of such a typical stream.

TABLE II

| Hydrocarbons, wt. % | | Sulfur Compound, wppm | |
|---|---|---|---|
| Ethane | 00.09 | $H_2S$ | 0.000 |
| Ethylene | 00.00 | Carbonyl Sulfide | 0.401 |
| Propane | 00.87 | Methyl Mercaptan | 0.756 |
| Propylene | 00.17 | Ethyl Mercaptan | 1.835 |
| Isobutane | 24.00 | Dimethyl Sulfide | 1.178 |
| n-butane | 22.73 | Dimethyl Disulfide | 1.057 |
| propadiene | 00.00 | Methylethyl Disulfide | 1.925 |
| Butene-1 | 20.08 | Diethyl Disulfide | 1.386 |
| Isobutene | 01.07 | Total Sulfur | 8.538 |
| t-Butene-2 | 17.96 | | |
| c-Butene-2 | 11.71 | | |
| Butadiene 1–3 | 0.04 | | |
| Isopentane | 01.16 | | |
| Pentene-1 | 00.06 | | |
| DME | 00.07 | | |
| Total Butenes | 50.81 | | |

The use of the distillation column reactor is known. Catalyst is placed on trays or combined into a distillation structure and placed into a distillation column. The selective hydrogenation of diolefins such as propadiene and 1–3 butadiene in a distillation column reactor is disclosed in U.S. Pat. No. 6,169,218 which is hereby incorporated by reference. In the present invention a fractional distillation is made simultaneously with the selective hydrogenation of the 1–3 butadiene to remove the DME contaminant as overheads.

The catalyst, to be effective, must be in the form so as to provide gas liquid contact. There are many forms of catalyst structures available for this purpose and these are disclosed variously in U.S. Pat. Nos. 5,266,546; 4,731,229; and 5,073,236. The most preferred catalyst structure is disclosed in U.S. Pat. No. 5,730,843 which is hereby incorporated by reference.

It is believed that in the present reactions catalytic distillation is a benefit first, because the reaction is occurring concurrently with distillation, the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up, but no increase in temperature at a given pressure. As a result, a great deal of control over the rate of reaction and distribution of products can be achieved by regulating the system pressure. Also, adjusting the throughput (residence time=liquid hourly space velocity$^{-1}$) gives further control of product distribution and to a degree control of the side reactions such as oligomerization. A further benefit that this reaction may gain from catalytic distillation is the washing effect that the internal reflux provides to the catalyst thereby reducing polymer build up and coking. Internal reflux may be varied over the range of 0.2 to 20 L/D (wt. liquid just below the catalyst bed/wt. distillate) and gives excellent results.

Referring now to the FIGURE a simplified flow diagram of the preferred embodiment of the invention is shown. The mixed $C_4$ stream is fed along with hydrogen via flow line 101 to a first distillation column reactor 10 containing a bed 12 of hydrogenation catalyst. In the distillation column reactor 10 the butadienes are selectively hydrogenated to butenes and at the same time the DME is separated by fractional distillation and removed as overheads via flowline 102. The bottoms containing the butenes and less than 10 wppm butadiene are removed via flow line 103 and fed to reactor 20 containing a bed 22 of catalyst that chemisorbs the sulfur compounds.

The effluent from the reactor 20 containing less than 1 wppm total sulfur compounds is removed via flow line 104 and fed, along with recycle from flow line 108, via flow line 105 to a second distillation column reactor 30 containing a bed 32 of ZSM-57 zeolite catalyst. A portion of the butenes in the stream are oligomerized to higher olefins, preferably octenes, in the catalyst bed. The higher boiling oligomers and some butenes are removed as bottoms via flow line 107. Some butenes may be taken as overheads and recycled as reflux (not shown) with a purge of lighter material taken via flow line 106 to prevent buildup of the lighter material.

The bottoms in flow line 107 are fed to a debutanizer column 40 where any $C_4$'s are removed as overheads and recycled to the second distillation column reactor 30 for further conversion. Product oligomers are removed from the debutanizer as bottoms via flow line 109 for further separation.

EXAMPLE 1

Twenty-one pounds of ZSM-57 zeolite catalyst were loaded in a distillation column reactor utilizing the catalyst structure shown in U.S. Pat. No. 5,730,843. A typical feed, as shown in TABLE II above, after treatment to remove the DME, butadiene and sulfur to acceptable levels was fed to the reactor. The reactor conditions and results are shown in TABLE III below.

TABLE III

| Hrs. on line | 392 | 640 | 742 | 804 | 888 |
|---|---|---|---|---|---|
| Feed, lbs/hr | 20 | 20 | 20 | 20 | 30 |
| Reflux, lbs/hr | 30 | 30 | 30 | 30 | 45 |
| Pressure, psig | 300 | 350 | 375 | 400 | 350 |
| Temp. ° F. | 245–255 | 271–286 | 274–289 | 293–313 | 299–317 |
| Upflow Conv. % | 66.68 | 93.88 | 97.03 | 98.23 | 86.88 |
| Select., wt. % | | | | | |
| $C_6$ olefins | 0.1286 | 0.2083 | 0.1612 | 0.2108 | 0.0912 |
| $C_8$ olefins | 96.6607 | 90.8567 | 92.8994 | 92.8113 | 93.3147 |
| $C_{10}$ olefins | 0.2383 | 0.5438 | 0.2862 | 0.2564 | 0.2371 |
| $C_{12}$ olefins | 2.9724 | 7.7808 | 6.4369 | 6.4651 | 6.2268 |
| $C_{12}$+ olefins | 0.000 | 0.6104 | 0.2164 | 0.2564 | 0.1302 |

EXAMPLE 2

The catalyst was regenerated in situ by washing with normal heptane under the following conditions:

TABLE IV

| Pressure, psig | 250 |
|---|---|
| Temperature, ° F. | 460 |
| n-heptane feed, lbs/hr | 15 |
| n-heptane overhead, lbs/hr | 10 |
| n-heptane bottoms, lbs · hr | 10 |
| catalyst, lbs | 21 |
| WHSV | 1.4 |
| Treatment time, hrs | 50 |

The mixed $C_4$ feed was restarted to the reactor and a comparison of the regenerated and fresh catalyst is shown in TABLE V below.

TABLE V

| Catalyst | Fresh | Regenerated |
|---|---|---|
| Feed, lbs/hr | 20 | 20 |
| Reflux, lbs/hr | 30 | 30 |
| Pressure, psig | 400 | 300 |
| Temp. ° F. | 293–313 | 220–230 |
| Upflow Conv. % | 98.23 | 99.95 |
| Select., wt. % | | |
| $C_6$ olefins | 0.2108 | 0.1931 |
| $C_8$ olefins | 92.8113 | 93.4661 |
| $C_{10}$ olefins | 0.2564 | 0.5570 |
| $C_{12}$ olefins | 6.4651 | 5.6407 |
| $C_{12}+$ olefins | 0.2564 | 0.1481 |
| Activity constant, k | 0.4696 | 2.7807 |
| Cat. Prod., g-mole/hr-lb cat | 2.5342 | 3.5278 |

Unexpectedly the regenerated catalyst performed better than the fresh catalyst.

The invention claimed is:

1. A process for the oligomerization of n-butenes comprising feeding n-butenes to a distillation column reactor, contacting said n-butenes in said distillation column reactor with a catalyst consisting of a bed of ZSM-57 zeolite catalyst, contacting said n-butenes with said ZSM-57 zeolite catalyst under conditions of oligomerization at pressures of between 300 and 400 psig and temperatures in the range of 240 to 320° F., thereby catalytically reacting said n-butenes to form oligomers and concurrently separating and recovering said oligomers.

2. The process for the oligomerization according to claim 1 comprising feeding a n-butenes stream to a distillation column reactor containing a bed of ZSM-57 zeolite catalyst, contacting said stream with said ZSM-57 zeolite catalyst by distillation, thereby catalytically reacting a portion of the n-butenes with themselves to form octenes and concurrently removing said octenes from said distillation column reactor as bottoms.

3. The process according to claim 2 wherein unreacted n-butenes are withdrawn from said distillation column reactor as overheads and a portion of said unreacted n-butenes is recycled to said distillation column reactor as reflux.

4. The process according to claim 2 wherein said bottoms contain unreacted n-butenes and said unreacted normal butenes are removed from said bottoms by fractional distillation and recycled to said distillation column reactor.

5. The process according to claim 2 wherein said stream has been treated to remove dimethyl ether, butadiene and organic sulfur compounds.

6. The process according to claim 5 wherein said stream contains less that 1 wppm dimethyl ether, less than 1 wppm organic sulfur compounds and less than 10 wppm butadiene.

7. The process according to claim 2 wherein the conversion of n-butenes is greater than 65 mol %, said dimers are octenes and the selectivity to said octenes is greater than 90 mol %.

8. The process according to claim 2 wherein the conversion of n-butenes is greater than 90 mol %, said dimers are octenes and the selectivity to said octenes is greater than 90 mol %.

9. The process according to claim 2 wherein said stream has been treated to remove dimethyl ether, butadiene and organic sulfur compounds.

10. The process according to claim 9 wherein said stream contains less that 1 wppm dimethyl ether, less than 1 wppm organic sulfur compounds and less than 10 wppm butadiene.

11. The process according to claim 2 wherein said catalyst has been poisoned by organic sulfur compounds to reduce its activity and selectivity and further comprising steps of stopping the feeding of said stream and washing said ZSM-57 zeolite catalyst with normal heptane and resuming the feeding of said stream.

12. The process according to claim 2 wherein said catalyst has been washed with normal heptane prior to feeding said stream.

13. The process according to claim 2 wherein the weight hourly space velocity is between 1 and 1.5 lbs of n- butenes per pound of catalyst.

14. The process according to claim 11 wherein said washing is carried out at about 4600° F., about 250° psig and about 1.4 lbs normal heptane per pound catalyst weight hourly space velocity for approximately 50 hours.

15. The orocess according to claim 2 wherein the n-butenes stream is obtained from a mixed $C_4$ stream containing dimethyl ether, butadienes, n-butenes, and organic sulfur compounds treated by a process comprising the steps of:

(a) feeding hydrogen and said mixed $C_4$ stream to a first distillation column reactor containing a bed of hydrogenation catalyst;

(b) concurrently in said first distillation column reactor:
  (i) contacting said mixed $C_4$ stream and hydrogen with said hydrogenation catalyst thereby selectively hydrogenating a portion of said butadienes and
  (ii) fractionating the resultant mixture of dimethyl ether and mixed $C_4$'s in said bed of hydrogenation catalyst;

(c) removing a portion of said dimethyl ether from said distillation column reactor as overheads;

(d) removing said mixed $C_4$'s from said distillation column reactor as bottoms, said bottoms being lower in dimethyl ether content and butadiene content;

(e) feeding said bottoms to a fixed bed reactor containing a chemisorption catalyst that selectively adsorbs organic sulfur compounds thereby removing a portion of said organic sulfur compounds; and (f) recovering the effluent from said fixed bed reactor as the stream containing n-butenes.

16. The process according to claim 15 wherein said bottoms contains less than 1 wppm dimethyl ether and less than 10 wppm butadienes and said effluent contains less than 1 wppm organic sulfur compounds.

17. The process according to claim 15 wherein said mixed $C_4$ stream is from a methyl ethyl tertiary butyl ether process or an isobutene purification process.

18. The process according to claim 17 wherein said mixed $C_4$ stream contains less that 10 mol% isobutene.

* * * * *